United States Patent
Alheidt

(10) Patent No.: US 10,070,969 B2
(45) Date of Patent: Sep. 11, 2018

(54) ANNULUS PLUG FOR INTERVERTEBRAL DISC REPAIR

(71) Applicant: Stryker European Holdings I, LLC, Kalamazoo, MI (US)

(72) Inventor: Thomas A. Alheidt, Sussex, NJ (US)

(73) Assignee: Stryker European Holdings I, LLC, Kalamazoo, MI (US)

(*) Notice: Subject to any disclaimer, the term of this patent is extended or adjusted under 35 U.S.C. 154(b) by 134 days.

(21) Appl. No.: 14/157,857

(22) Filed: Jan. 17, 2014

(65) Prior Publication Data

US 2014/0200672 A1 Jul. 17, 2014

Related U.S. Application Data

(60) Provisional application No. 61/753,649, filed on Jan. 17, 2013.

(51) Int. Cl.
| | | |
|---|---|---|
| *A61F 2/44* | (2006.01) | |
| *A61F 2/28* | (2006.01) | |
| *A61F 2/30* | (2006.01) | |
| *A61F 2/46* | (2006.01) | |

(52) U.S. Cl.
CPC ............ *A61F 2/4455* (2013.01); *A61F 2/442* (2013.01); *A61F 2002/2835* (2013.01); *A61F 2002/30405* (2013.01); *A61F 2002/4435* (2013.01); *A61F 2002/4677* (2013.01)

(58) Field of Classification Search
CPC .............. A61F 2/4455; A61F 2002/448; A61F 2002/2835; A61F 2220/0025; A61F 2002/4629; A61F 2002/30507; A61F 2220/0033; A61F 2/46; A61F 2/4637
USPC .... 623/17.11, 17.16; 606/246–249, 300–320
See application file for complete search history.

(56) References Cited

U.S. PATENT DOCUMENTS

| | | | |
|---|---|---|---|
| 5,098,434 A | * | 3/1992 | Serbousek ......... A61B 17/8625 606/308 |
| 5,192,283 A | * | 3/1993 | Ling ................... A61B 17/164 606/92 |
| 6,224,630 B1 | | 5/2001 | Bao et al. |
| 6,425,919 B1 | | 7/2002 | Lambrecht |
| 6,482,235 B1 | | 11/2002 | Lambrecht et al. |
| 6,508,839 B1 | | 1/2003 | Lambrecht et al. |
| 6,719,794 B2 | | 4/2004 | Gerber et al. |
| 6,733,531 B1 | | 5/2004 | Trieu |
| 6,821,276 B2 | | 11/2004 | Lambrecht et al. |
| 6,878,167 B2 | | 4/2005 | Ferree |
| 6,936,072 B2 | | 8/2005 | Lambrecht et al. |
| 6,964,674 B1 | | 11/2005 | Matsuura et al. |
| 6,974,480 B2 | | 12/2005 | Messerli et al. |
| 7,004,970 B2 | | 2/2006 | Cauthen, III et al. |

(Continued)

FOREIGN PATENT DOCUMENTS

EP 2140841 A1 1/2010

*Primary Examiner* — Eduardo C Robert
*Assistant Examiner* — Tara R Carter
(74) *Attorney, Agent, or Firm* — Lerner, David, Littenberg, Krumholz & Mentlik, LLP

(57) ABSTRACT

A device for intervertebral disc repair includes a cannulated screw having a head and a shaft, a plug defining an aperture, and an intervertebral spacer. The screw is configured to be placed through the aperture and into engagement with the spacer. A kit includes the device, a guide wire connectable with the spacer, and a bone tamp. Methods of using the device and kit are provided.

29 Claims, 3 Drawing Sheets

(56) References Cited

U.S. PATENT DOCUMENTS

| | | | |
|---|---|---|---|
| 7,198,047 B2 | 4/2007 | Lambrecht et al. |
| 7,223,227 B2 | 5/2007 | Pflueger |
| 7,258,700 B2 | 8/2007 | Lambrecht et al. |
| 7,318,840 B2 | 1/2008 | McKay |
| 7,445,634 B2 | 11/2008 | Trieu |
| 7,507,243 B2 | 3/2009 | Lambrecht et al. |
| 7,553,329 B2 | 6/2009 | Lambrecht et al. |
| 7,618,456 B2* | 11/2009 | Mathieu ............. A61B 17/8052 623/17.11 |
| 7,658,765 B2 | 2/2010 | Lambrecht et al. |
| 7,682,394 B2 | 3/2010 | Recoules-Arche et al. |
| 7,717,961 B2 | 5/2010 | Lambrecht et al. |
| 7,749,273 B2 | 7/2010 | Cauthen, III et al. |
| 7,857,855 B2 | 12/2010 | Ferree |
| 7,879,097 B2 | 2/2011 | Lambrecht et al. |
| 7,972,337 B2 | 7/2011 | Boyajian et al. |
| 8,025,697 B2 | 9/2011 | McClellan, III et al. |
| 8,025,698 B2 | 9/2011 | Lambrecht |
| 8,034,110 B2 | 10/2011 | Garner et al. |
| 8,114,161 B2 | 2/2012 | Evans et al. |
| 8,221,460 B2 | 7/2012 | Mathews |
| 8,231,678 B2 | 7/2012 | Lambrecht |
| 8,273,110 B2 | 9/2012 | Seifert et al. |
| 8,308,803 B2 | 11/2012 | Foley et al. |
| 8,323,341 B2 | 12/2012 | Lambrecht et al. |
| 2002/0029083 A1 | 3/2002 | Zucherman et al. |
| 2002/0065518 A1* | 5/2002 | Naybour ............. A61F 2/4601 606/86 R |
| 2002/0138146 A1* | 9/2002 | Jackson ............. A61F 2/4455 623/17.15 |
| 2002/0147461 A1 | 10/2002 | Aldrich et al. |
| 2002/0147497 A1 | 10/2002 | Belef et al. |
| 2003/0114930 A1 | 6/2003 | Lim et al. |
| 2004/0010317 A1 | 1/2004 | Lambrecht et al. |
| 2004/0024465 A1 | 2/2004 | Lambrecht et al. |
| 2004/0044412 A1 | 3/2004 | Lambrecht et al. |
| 2004/0143334 A1 | 7/2004 | Ferree |
| 2004/0210310 A1 | 10/2004 | Trieu |
| 2004/0260397 A1 | 12/2004 | Lambrecht et al. |
| 2005/0101960 A1* | 5/2005 | Fiere ............. A61B 17/7059 623/17.11 |
| 2005/0159817 A1 | 7/2005 | Ferree |
| 2005/0206039 A1 | 9/2005 | Lambrecht et al. |
| 2005/0256582 A1 | 11/2005 | Ferree |
| 2006/0195193 A1 | 8/2006 | Bloemer et al. |
| 2007/0118133 A1 | 5/2007 | Lambrecht et al. |
| 2007/0135921 A1 | 6/2007 | Park |
| 2007/0150064 A1 | 6/2007 | Ruberte et al. |
| 2007/0282441 A1* | 12/2007 | Stream ............. A61B 17/92 623/17.11 |
| 2008/0065218 A1 | 3/2008 | O'Neil |
| 2008/0249625 A1* | 10/2008 | Waugh ............. A61F 2/4465 623/17.16 |
| 2010/0004747 A1* | 1/2010 | Lin ............. A61B 17/7059 623/17.16 |
| 2010/0049259 A1 | 2/2010 | Lambrecht et al. |
| 2010/0145397 A1* | 6/2010 | Overes ............. A61B 17/68 606/319 |
| 2011/0160866 A1* | 6/2011 | Laurence ............. A61B 17/1671 623/17.16 |
| 2011/0196492 A1 | 8/2011 | Lambrecht et al. |
| 2011/0245923 A1 | 10/2011 | Cobb et al. |
| 2011/0251689 A1* | 10/2011 | Seifert ............. A61F 2/442 623/17.16 |
| 2012/0158144 A1* | 6/2012 | Ullrich, Jr. ............. A61F 2/447 623/17.16 |
| 2012/0232665 A1 | 9/2012 | Godara et al. |
| 2012/0316648 A1 | 12/2012 | Lambrecht et al. |
| 2012/0316654 A1 | 12/2012 | Seifert et al. |
| 2013/0053964 A1* | 2/2013 | Talwar ............. A61F 2/442 623/17.16 |
| 2013/0150969 A1* | 6/2013 | Zipnick ............. A61F 2/44 623/17.16 |

* cited by examiner

ANNULUS PLUG FOR INTERVERTEBRAL DISC REPAIR

CROSS-REFERENCE TO RELATED APPLICATIONS

The present application claims the benefit of the filing date of U.S. provisional patent application No. 61/753,649 filed Jan. 17, 2013, the disclosure of which is hereby incorporated herein by reference.

BACKGROUND OF THE INVENTION

The present invention relates to intervertebral disc replacement procedures and devices used in such a procedures. A purpose of the invention is to compress bone graft material within the disc space and also to prevent any bone graft material from migrating out of the disc space after an interbody fusion device is implanted therein. More particularly, the present invention includes an anchor screw inserted through a plate or plug and connected with an interbody fusion device.

In existing intervertebral disc replacement procedures, an opening or hole is created in the annulus fibrosis surrounding the disc space to create an access portal into the disc space for introduction of one or more devices after the disc space is initially cleared. After the introduction of the device(s), it is a common procedure to fill the remaining open area of the disc space with bone graft material to provide additional structure to the disc space and to promote bone growth between the adjacent vertebral bodies.

However, the hole created in the annulus typically remains partially or fully open after the procedure. In some instances, the hole can be closed in such a way that does not substantially prevent the movement and/or migration of the bone graft material from its implanted location. The closure of the annulus, even if sealed in a generally effective manner, may require some open space within the disc space adjacent the hole in the annulus in order to properly use certain instruments to complete the procedure. As a result, the implanted bone graft material is not sealed within the disc space and/or is not packed tightly enough into its implanted location. The bone graft material can then be subject to movement and even migration out of the disc space through the area of the annulus opened for initial access to the disc space.

In addition, any biologic material provided to the disc space during the procedure is subject to migration out through the hole in the annulus. This can potentially create a situation in which the biologic is located in areas outside of the repaired disc space that are not intended or even able to support bone growth.

Therefore, there is a need for a device that more securely closes the access hole created in the annulus during an intervertebral disc replacement procedure to ensure that the materials inserted into the disc space after that procedure remain firmly in place and do not migrate or shift to undesired degrees. Methods of using such devices and methods that more securely close and pack the disc space after an intervertebral disc replacement procedure are also needed.

SUMMARY OF THE INVENTION

A first aspect of the present invention is a device for intervertebral disc repair including a cannulated screw having a head and a shaft, a plug defining an aperture, and an intervertebral spacer. The screw is configured to be placed through the aperture and into engagement with the spacer.

In accordance with other embodiments of the first aspect, the shaft can be at least partially threaded. The aperture of the plug can include a seat, and the head of the screw can include a complimentary surface to interface with the seat of the plug. An outer periphery of the plug can be circular or square shaped. The spacer can include an aperture for engagement with the screw. The aperture of the spacer can be cylindrically shaped about a first axis that forms a non-zero acute angle with respect to a second axis extending through leading and trailing ends of the spacer. The aperture of the spacer can be disposed on a lateral side of the spacer. The spacer can be comprised of a first material and the aperture of the spacer can be lined with a second material different than the first material. An outer periphery of the plug can include an annular groove. The device can further include an annular element including a biologic material disposed around a portion of the shaft of the screw. The spacer and the plug can each be comprised of a polymeric material.

A second aspect of the present invention is a kit for intervertebral disc repair including a device, a guide wire, and a bone tamp. The device includes a cannulated screw having a head and a shaft, a plug defining an aperture, and an intervertebral spacer. The screw is configured to be placed through the aperture and into engagement with the spacer. The guide wire is connectable with the spacer.

A third aspect of the present invention is a method for intervertebral disc repair including inserting an intervertebral spacer into a disc space through a hole formed in the annulus, inserting bone graft material into the disc space, placing a plug into or adjacent the hole formed in the annulus, the plug defining an aperture, inserting a screw through the aperture, and connecting the screw to the spacer.

In accordance with other embodiments of the third aspect, the method can further include connecting a guide wire with the spacer, and the step of inserting the screw can include inserting a cannulated portion of the screw over the guide wire. The method can further include packing the bone graft material into the disc space with a cannulated bone tamp provided over the guide wire. The step of placing the plug can include inserting the aperture of the plug over the guide wire. The method can further include packing the bone graft material into the disc space with a bone tamp. The step of connecting the screw to the spacer can include threading a distal portion of the screw into an aperture in the spacer. The steps of placing the plug and inserting the screw can compress the bone graft material within the disc space. The step of placing the plug can prevent the bone graft from migrating out of the disc space.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for fixation of spinal vertebrae. Those of skill in the art will recognize that the following description is merely illustrative of the principles of the invention, which may be applied in various ways to provide many different alternative embodiments.

Figure 1:
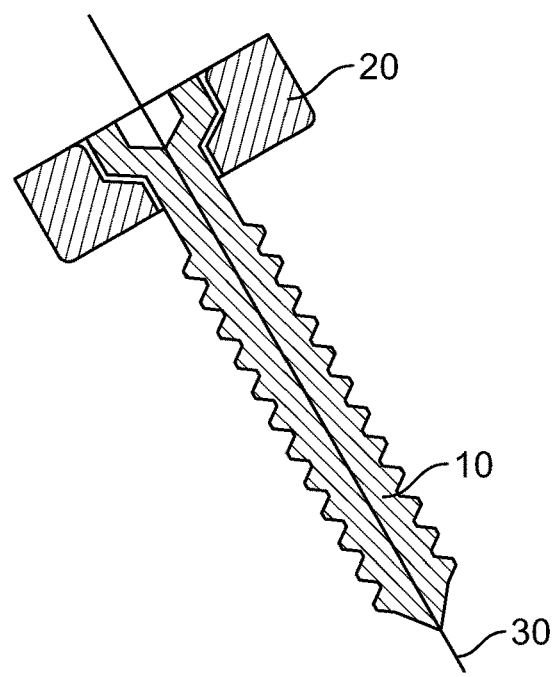
FIG. 1 is a sectional view of a screw, an annulus plug, and a guide wire in accordance with an embodiment of the present invention.

In an embodiment of the present invention as shown in FIG. 1, a screw 10 is provided with an annulus plug 20. Screw 10 is cannulated, has a head, and includes a shaft that can be fully or at least partially threaded. The unthreaded portion of the shaft can be at the distal and/or the proximal portion of screw 10. The head of screw 10 preferably includes a tapered surface or other complimentary surface or feature on its distal portion to engage with plug 20.

Plug 20 is a generally annular or ring-shaped element, having an aperture in its central portion for receipt of screw 10. The aperture can have a seat that may be tapered or otherwise configured to accept the complimentary configuration of the head of screw 10. Such configuration can be tapered, stepped, etc. to allow for screw 10 to be inserted to a particular depth within the aperture of plug 20. The outer periphery of plug 20 can be circular, square shaped, or any other shape in order to provide a secure closure and mating fit with the hole created in the annulus. In this regard, it is contemplated to construct plug 20 of a material that can be trimmed or otherwise modified to fit within or adjacent to a particular hole in the annulus. A guide wire 30 is also shown in FIG. 1 and extends through the cannulated portion of screw 10 and the aperture of plug 20.

Figure 2:
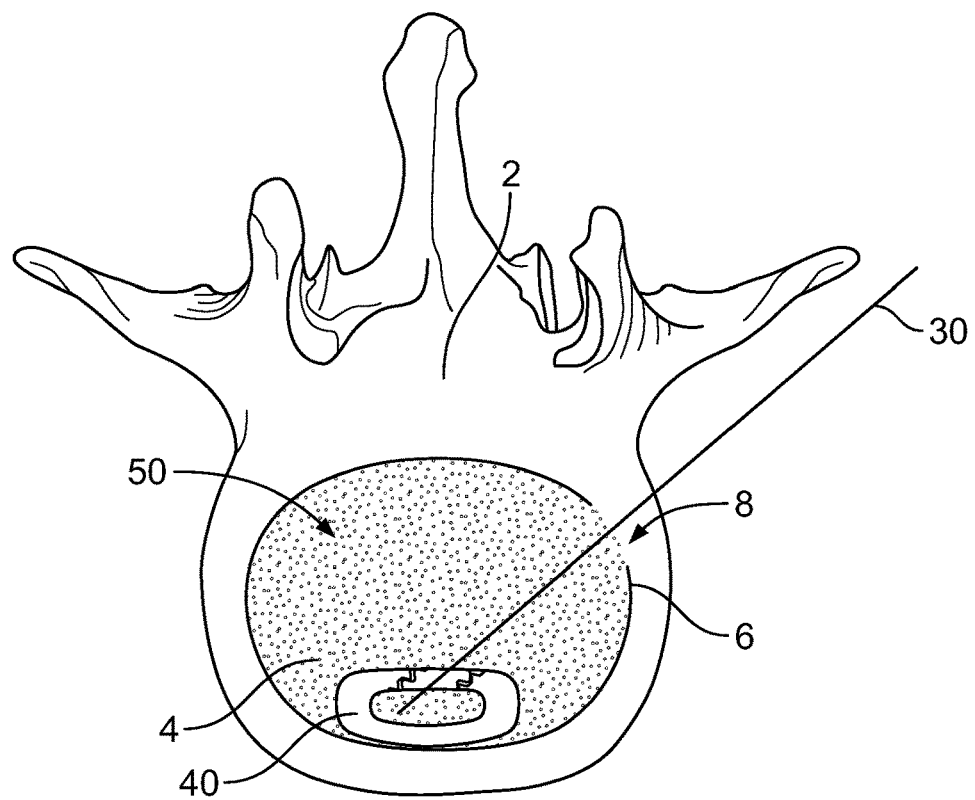
FIG. 2 is a top plan view of a spacer adjacent a vertebral body in accordance with an embodiment of the present invention.

FIG. 2 is a top plan view of a vertebral body 2 and an intervertebral disc space 4. An annulus 6 surrounds the disc space 4, and is interrupted by a hole 8 through which a surgical procedure of inserting an interbody fusion device or spacer 40 is performed. Spacer 40 is located in the anterior portion of disc space 4, and the remainder of disc space 4 is provided with bone graft material 50.

As shown in FIG. 2, a first step of the present procedure is the insertion of spacer 40 into the disc space 4 through a previously created hole 8 in annulus 6. Guide wire 30 is preferably connected with spacer 40 either before or after its insertion into disc space 4. To create such a connection, guide wire 30 can be attached in any suitable manner to spacer 40, such as being wrapped around a portion of spacer 40, embedded into a portion of spacer 40, kinked or knotted within an opening in spacer 40, attached with an anchor disposed within an opening in spacer 40, or by any other known method of securely but removably creating such a connection. After spacer 40 is implanted, preferably into its final position, disc space 4 is packed with bone graft material 50. Material 50 is provided in and/or around spacer 40 within the confines of the disc space 4 defined by annulus 6. The bone graft material used in connection with the present invention can be any suitable material that promotes bone growth, such as demineralized bone matrix (DBM), autograft bone tissue, allograft bone tissue, bone morphogenic protein (BMP), for example. The bone graft material can be in any suitable form, such as liquid or solid.

Figure 3:
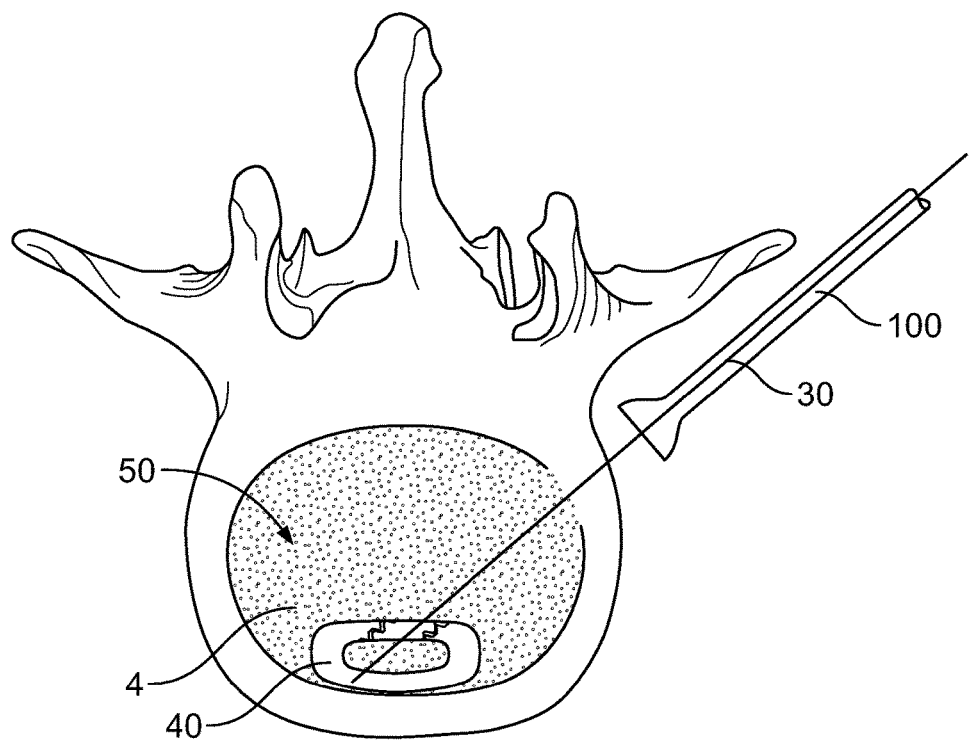
FIG. 3 is a top plan view of the spacer adjacent the vertebral body shown in FIG. 2 and also showing a bone tamp in accordance with a method of the present invention.

FIG. 3 shows another step of the procedure in which a cannulated bone tamp 100 is used over guide wire 30 to tightly pack bone graft material 50 into the confines of disc space 4. Tamp 100 could alternatively be provided without a cannula, in which case it could be used without the guidance of guide wire 30. The result of this step is that bone graft material 50 is further compressed within disc space 4.

Figure 4:
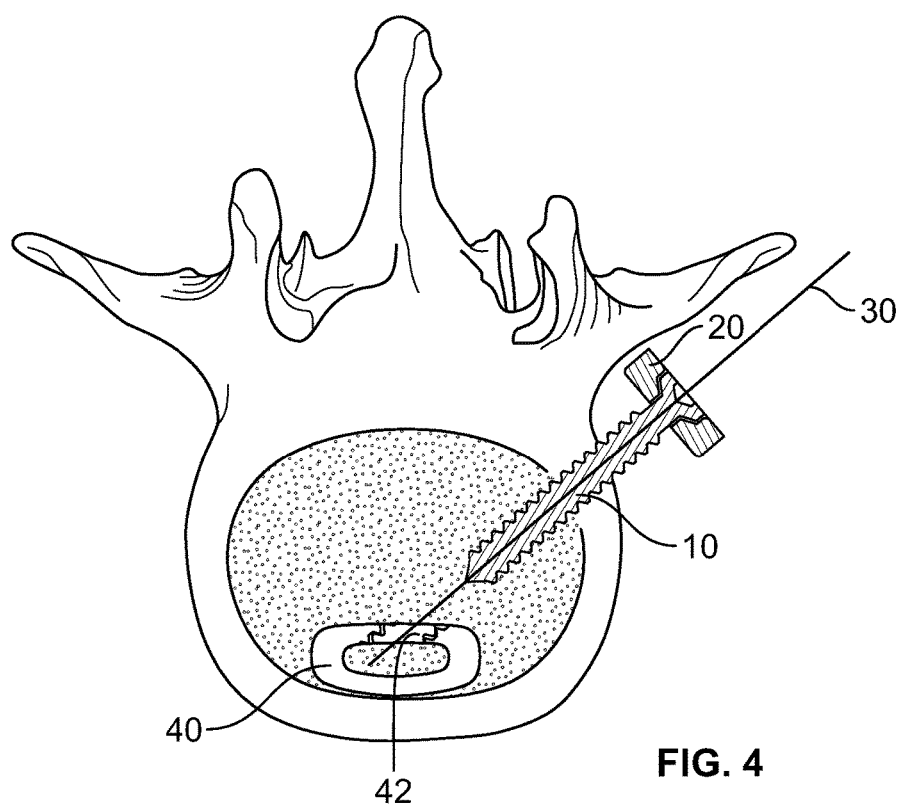
FIGS. 4 and 5 are top plan views of the spacer adjacent the vertebral body shown in FIG. 2 and also showing the screw and annulus plug shown in FIG. 1.

A further step of the procedure shown in FIG. 4, in which screw 10 and plug 20 are inserted over guide wire 30 such that the distal portion of screw 10 is moved into disc space 4. The distal portion of screw 10, which is preferably threaded, is moved into connection with an aperture 42 in spacer 40. Aperture 42 can be provided in spacer 40 in any location thereof that is conducive to fixing screw 10 with spacer 40 from the direction of the hole 8 in annulus 6. The location of aperture 42 can therefore be designed and configured in connection with the intended finally implanted location of spacer 40 with respect to the intended location of hole 8 in annulus 6, through which screw 10 will be provided. Thus, the configuration of aperture 42 in spacer can vary according to need. Alternatively, spacer 40 could include multiple apertures 42. In the preferred embodiment of FIGS. 2-5, aperture 42 is cylindrically shaped and is disposed along an axis at a non-zero acute angle with respect to a longitudinal axis of the spacer extending through the leading and trailing ends thereof. Aperture 42 can be located at a lateral side portion of spacer 40, and is not required to be disposed at a leading or trailing end thereof. Aperture 42 can extend partially or fully into spacer 40, and may simply be provided within spacer 40 or maybe lined with a more sturdy material or sleeve of material to provide for a more firm connection with the threads of screw 10.

Figure 5:
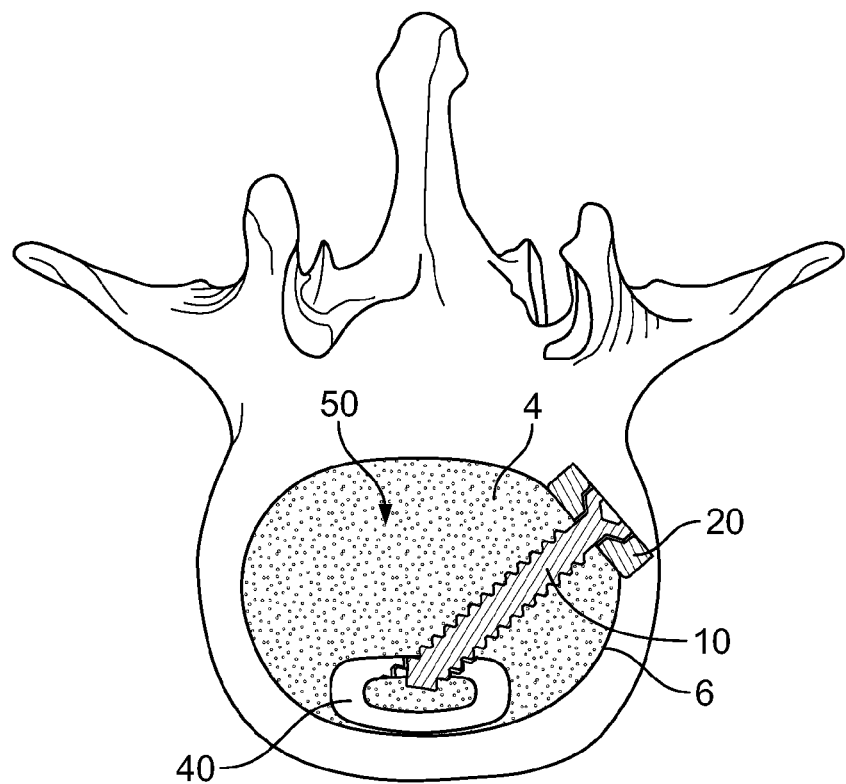

As shown in FIG. 5, the screw 10 and plug 20 construct can be inserted to a finally implanted location in which plug 20 is essentially flush with the outer portion of annulus 6. In such a preferred embodiment, the configuration of plug 20 is such that it has an outer periphery sized to completely overlap the outer periphery of hole 8. In other embodiments, the outer periphery of plug 20 may be configured to substantially match the size and shape of hole 8, such that plug 20 fits within and fills hole 8. Either configuration may require an irregularly shaped periphery of plug 20 according to the configuration of hole 8 in annulus 6, and any such periphery is possible as dictated by the needs of a particular procedure and patient anatomy. In the preferred embodiment, the cross sectional area of the plug 20 and screw 10 construct in a plane perpendicular to the axis of the screw is greater than the surface area of hole 8 in annulus 6, permitting the plug 20 and screw 10 construct to fully cover hole 8 and enclose disc space 4. Thus, in the preferred embodiment, plug 20 is disposed against at least a portion of the outer surface of annulus 6 adjacent hole 8 in its implanted position. In other embodiments, such as an embodiment in which the outer periphery of plug 20 matches the size and shape of hole 8, plug 20 may be disposed against the bone graft material 50 packed within disc space 4 in its final implanted position.

Once plug 20 is seated against annulus 6, screw 10 is tightened to ensure a firm connection between plug 20 and spacer 40. As discussed above, plug 20 may be configured such that its distal surface overlaps and presses against annulus 6. The height and width of plug 20 is preferably at least the same size as the hole 8 in annulus 6, and may be slightly larger to overlap hole 8. In other embodiments, plug 20 can have a periphery including a horizontal groove so that proximal and distal portions of plug 20 can be positioned in respective proximal and distal locations with respect to the annulus 6, such that the portion of the annulus 6 defining hole 8 is seated within the groove. Plug 20 can be placed into its final position in a separate step from the insertion of screw 10, which can thereafter be advanced along guide wire 30, through plug 20, and into connection with spacer 40. The distal portion of screw 10 is screwed into aperture 42 of spacer 40. As the head of screw 10 fills the aperture in plug 20, this creates a fully closed annulus 6.

As screw 10 is rotated about the guide wire into it final position, plug 20 can either rotate along with screw 10 or can remain stationary with respect to annulus 8. Although the screw 10 may impart a pulling force on spacer 40 during insertion and engagement, such forces do not substantially alter the finally implanted location of spacer 40. This can at least be due in part to structures on spacer 40, which aid in retaining its position, such as teeth, ridges, grooves, or other similar structures on at least the surfaces of spacer 40 that contact and interact with the adjacent vertebrae.

The cannulated portion of screw 10 can be plugged by a separate element (not shown) after the procedure to fully close access to disc space 4. After insertion of screw 10, guide wire 30 is removed. Before or after plugging screw 10, guide wire 30 can be cut or otherwise removed from the space distal of screw 10 and plug 20.

As screw 10 is inserted into the already tightly packed disc space, the space occupied by the inserted screw 10 displaces bone graft material 50, which further compresses all of the materials and components residing within disc space 4. The displacement of the volume of all components inserted into disc space 4 continues to pack bone graft material 50 further into the disc space until such components are finally implanted. Accordingly, screw 10 can be configured to occupy greater or lesser amounts of volume as necessary. This can include a conically tapered exterior surface of screw 10 so that the displaced volume increases as the screw is inserted. The closure of hole 8 in annulus 6 as well as any displacement of volume within disc space 4 is aimed at packing bone graft material 50 and any other components within disc space 4 as tightly as possible to allow all components within disc space 4 to be positioned to inhibit movement thereof after the surgical procedure is concluded. This provides for a more stable and surgically repaired disc space to allow bone growth to occur as immediately as possible after the procedure is concluded. The more stable the environment within disc space 4, the less migration of components therein and the more likely and immediate the subsequent bone growth.

In certain embodiments, the height of plug 20 is at least the same as the height of spacer 40, which allows plug 20 to further provide stability between the portions of the adjacent vertebrae with which it contacts. As indicated above, the distal end of screw 10 can be inserted into a sleeve located in spacer 40 to allow the screw 10 to be delivered without damaging the material of spacer 40.

Figure 6:
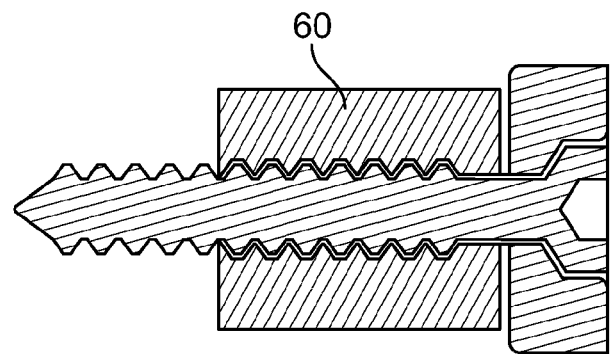
FIG. 6 is a sectional view of a screw, an annulus plug, and a biologic as an annular element disposed around a portion of a shaft of the screw in accordance with another embodiment of the present invention.

Screw 10 can be packaged to include biologics that act during the procedure to further displace volume within the disc space 4 and compress bone graft material 50 within disc space 4 to stimulate bone growth. Such a biologic 60 is shown in FIG. 6 as an annular element disposed around a portion of the shaft of screw 10. Of course, biologics can be provided in any form, including solid or liquid, such that they are disposed within the disc space 4 after final implantation of screw 10 and closure of annulus 6. This includes biologic such as biologic which is located about screw, or can also include other biologic materials disposed elsewhere in disc space 4. Such materials can include BMP, DBM, or any other type of bone stimulator. Biologics can be included prior to insertion of bone graft material 50, during insertion thereof, afterward and just prior to insertion of screw 10 and plug 20.

As indicated above, guide wire 30 can be attached to spacer 40 to guide the insertion of screw 10 as well as the tamping action of cannulated bone tamp 100. The connection between guide wire 30 and spacer 40 can be made prior to insertion of spacer 40 or during the procedure after spacer 40 is implanted. Suitable connections include threaded or interference connections, quick connect mechanisms, or other known commonly used connection mechanisms.

Spacer 40 and plug 20 are each preferably constructed of a biocompatible such as a polymeric material, for example, polyetheretherketone ("PEEK"). Other biocompatible materials can be used to construct spacer 40 and/or plug 20, such as polyethylene or other polymeric materials, allograft bone tissue, autograft bone tissue, metal such as titanium, and ceramic. However, spacer 40 and plug 20 may be constructed of practically any materials suitable for implantation in the body of a human. Two or more materials can be used to construct spacer 40 and/or plug 20, and stronger materials can be used in specific aspects of either element as necessary. The lining of aperture 42 in spacer 40 can be comprised of any biocompatible material, such as metal, ceramic, or polymer. Preferably, the material that comprises a lining is of greater strength than the material from which spacer 40 and/or plug 20 is constructed to enhance the strength of the final construct. Screw 10 is preferably made of a metallic material, such as titanium. It is within the scope of this disclosure that other materials may be used for the various components of the invention as long as such materials are configured to achieve the intended stabilized results of the construct.

While the aforementioned invention is described in connection with the method of inserting, the components themselves also contributed to the novelty of the present invention. In that regard, certain novel aspects of the present invention include, but are not limited to: plug 20; a construct including plug 20 and screw 10; spacer 40 including aperture 42; spacer 40 including aperture 42 lined with a metallic material or sleeve; spacer 40 in connection with guide wire 30; a kit including screw 10, spacer 40, guide wire 30, and plug 20; and a method of inserting any or all of the above described components.

The method described above and shown in the figures utilizes a transforaminal lumbar interbody fusion (TLIF) technique. Other techniques are possible, such as a posterior lumbar interbody fusion (PLIF) technique. In addition, more than one construct including a spacer, a screw, and a plug can be implanted into a disc space to complete a single procedure. Such might be the case if a PLIF technique is employed, with two separate constructs being inserted on each side of the disc space, with access for each respective construct being located on either side of the central spinous process. Furthermore, spacers according to the present invention can be constructed to provide a lordotic force to the adjacent vertebrae.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

The invention claimed is:

1. A device for intervertebral disc repair comprising:
   a cannulated screw having a head and a shaft;
   a plug defining an aperture; and
   an intervertebral spacer having a proximal end and a distal end, and defining an aperture disposed on a laterally-facing surface of the spacer,
   wherein a height of the plug is substantially equal to a height of the spacer,
   wherein the screw is configured to be placed through the aperture of the plug and into engagement with the spacer, and
   wherein the aperture of the spacer is cylindrically shaped about a first axis that forms a non-zero acute angle with respect to a second axis extending through the proximal and distal ends of the spacer.

2. The device of claim 1, wherein the shaft is at least partially threaded.

3. The device of claim 1, wherein the aperture of the plug includes a seat, and the head of the screw includes a complimentary surface to interface with the seat of the plug.

4. The device of claim 1, wherein a shape of an outer periphery of the plug is a circle or a square.

5. The device of claim 1, wherein the spacer is comprised of a first material and the aperture of the spacer is lined with a second material different than the first material.

6. The device of claim 1, wherein an outer periphery of the plug includes an annular groove.

7. The device of claim 1, further comprising an annular element including a biologic material disposed around a portion of the shaft of the screw.

8. The device of claim 1, wherein the spacer and the plug are each comprised of a polymeric material.

9. A kit for intervertebral disc repair comprising:
   the device of claim 1;
   a guide wire connectable with the spacer;
   a bone tamp.

10. The device of claim 1, wherein the height of the plug is a maximum height measured between superior-most and inferior-most ends of the plug.

11. A method for intervertebral disc repair comprising:
    inserting an intervertebral spacer into a disc space through a hole formed in the annulus;
    inserting bone graft material into the disc space;
    placing a plug into the hole formed in the annulus, the plug defining an aperture, while maintaining a space between the spacer and the plug;
    inserting a screw through the aperture; and
    connecting the screw to the spacer,
    wherein the steps of placing the plug and inserting the screw occur after the step of inserting the intervertebral spacer into the disc space.

12. The method of claim 11, further comprising:
    connecting a guide wire with the spacer;
    wherein the step of inserting the screw includes inserting a cannulated portion of the screw over the guide wire.

13. The method of claim 12, further comprising:
    packing the bone graft material into the disc space with a cannulated bone tamp provided over the guide wire.

14. The method of claim 12, wherein the step of placing the plug includes inserting the aperture of the plug over the guide wire.

15. The method of claim 11, further comprising:
    packing the bone graft material into the disc space with a bone tamp.

16. The method of claim 11, wherein the step of connecting the screw to the spacer includes threading a distal portion of the screw into an aperture in the spacer.

17. The method of claim 11, wherein the steps of placing the plug and inserting the screw compress the bone graft material within the disc space.

18. The method of claim 11, wherein the step of placing the plug prevents the bone graft from migrating out of the disc space.

19. The method of claim 11, wherein the step of inserting bone graft material into the disc space occurs after the step of inserting the spacer into the disc space, and includes placing the bone graft material around and outside of the spacer.

20. A method for intervertebral disc repair comprising:
    inserting an intervertebral spacer into a disc space through a hole formed in the annulus;
    connecting a guide wire with the spacer;
    inserting bone graft material into the disc space;
    packing the bone graft material into the disc space with a cannulated bone tamp provided over the guide wire;
    placing a plug into or adjacent the hole formed in the annulus, the plug defining an aperture;
    inserting a screw through the aperture, including inserting a cannulated portion of the screw over the guide wire; and
    connecting the screw to the spacer.

21. A device for intervertebral disc repair comprising:
    a plug defining an aperture;
    an intervertebral spacer having a proximal end and a distal end, and defining an aperture disposed on a laterally-facing surface of the spacer; and
    a cannulated screw having a head and a shaft, wherein when the device is in an implanted configuration, the shaft is placed through the aperture of the plug and into engagement with the aperture of the spacer such that the plug and the spacer are separated by a space that is maintained by the screw, and
    wherein the aperture of the spacer is cylindrically shaped about a first axis that forms a non-zero acute angle with respect to a second axis extending through the proximal and distal ends of the spacer.

22. The device of claim 21, wherein the shaft is at least partially threaded.

23. The device of claim 21, wherein the aperture of the plug includes a seat, and the head of the screw includes a complimentary surface to interface with the seat of the plug.

24. The device of claim 21, wherein a shape of an outer periphery of the plug is a circle or a square.

25. The device of claim 21, wherein the spacer is comprised of a first material and the aperture of the spacer is lined with a second material different than the first material.

26. The device of claim 21, wherein an outer periphery of the plug includes an annular groove.

27. The device of claim 21, further comprising an annular element including a biologic material disposed around a portion of the shaft of the screw.

28. The device of claim 21, wherein the spacer and the plug are each comprised of a polymeric material.

29. A kit for intervertebral disc repair comprising:
    the device of claim 21;
    a guide wire connectable with the spacer;
    a bone tamp.

* * * * *